United States Patent [19]
Bader

[11] 3,949,197
[45] Apr. 6, 1976

[54] METHODS AND APPARATUSES FOR CORRECTING COINCIDENCE COUNT ERRORS IN A PARTICLE ANALYZER HAVING A SENSING ZONE THROUGH WHICH THE PARTICLES FLOW

[75] Inventor: Henri Bader, Miami, Fla.
[73] Assignee: Coulter Electronics, Inc., Hialeah, Fla.
[22] Filed: Sept. 26, 1972
[21] Appl. No.: 292,421

[52] U.S. Cl.......... 235/92 PC; 235/92 R; 324/71 CP
[51] Int. Cl.².................. G01N 27/00; G06M 11/00
[58] Field of Search................ 235/92 PC, 92 EC; 324/71 CP

[56] References Cited
UNITED STATES PATENTS
3,444,463  5/1969  Coulter........................ 235/92 PC
3,502,974  3/1970  Coulter........................ 324/71 CP Primary Examiner—Joseph M. Thesz, Jr.
Attorney, Agent, or Firm—Silverman & Cass, Ltd.

[57] ABSTRACT

By creating at least two related raw counts $n$ and $n_i$, of particles in a fluid suspension as at least two physically derived particle counts, there can be developed a mathematic function relationship by which the "scanning constant" $k$ of a particle analyzer, for example of a Coulter type, can be factored out and a resultant equation obtained. The resultant equation is employable, for instance, in operating upon the input $n$ and $n_i$ raw counts for generating the ultimately desired corrected particle count $N_i$ which largely eliminates particle coincidence errors. The disclosure encompasses several methods and apparatuses by which the raw counts are developed and by which the related mathematic functions are defined and then employed to obtain corrected counts. Specially considered are multichannel analysis and optical apparatus for facilitating the count correction.

32 Claims, 6 Drawing Figures

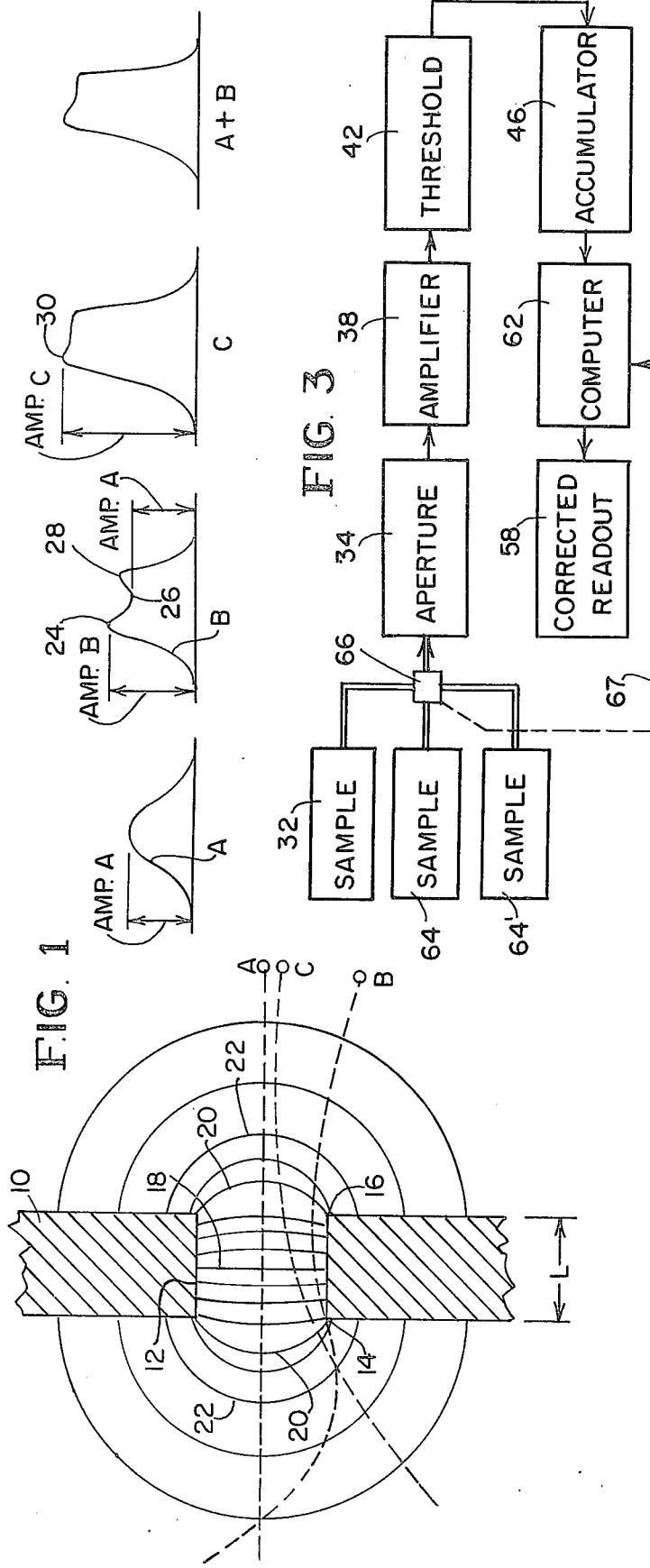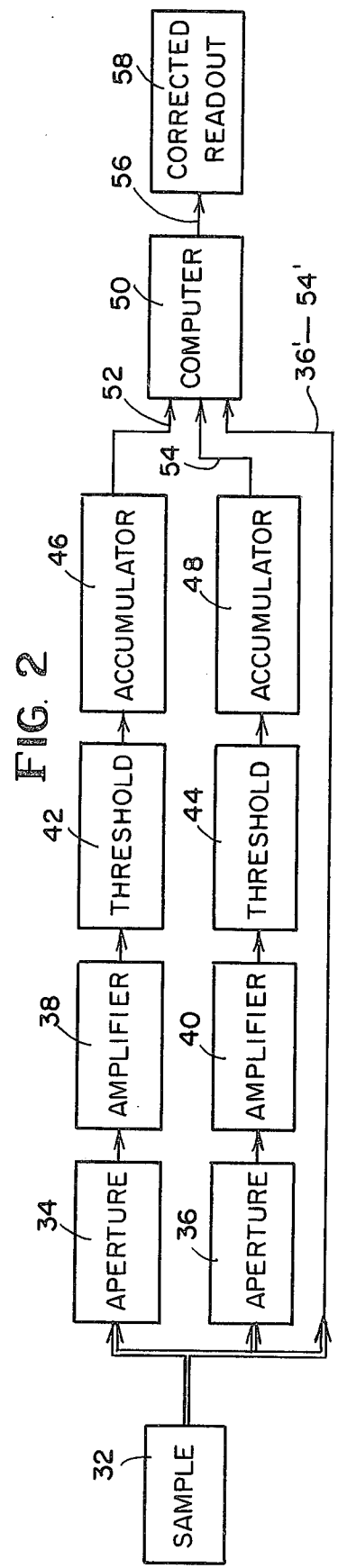

METHODS AND APPARATUSES FOR CORRECTING COINCIDENCE COUNT ERRORS IN A PARTICLE ANALYZER HAVING A SENSING ZONE THROUGH WHICH THE PARTICLES FLOW

BACKGROUND OF THE INVENTION

This invention is directed to particle counting methods and apparatuses which provide a statistic correction to a detected train of particle derived count pulses, such that effective random coincidence loss or gain of count does not induce ultimate counting error.

The particle counting methods and apparatuses concerned employ particle sensing zones in which more than one particle might reside at any one time and thereby randomly generate a coincidence condition. This invention particularly is directed to, but not limited to the determination of non-electrical properties, such as size and count of particles, by measuring electrical properties (Patent Office class 324-71NE).

Now well known in the art of electronic particle counting and analyzing is apparatus marketed primarily under the trademark "Coulter Counter". Such apparatus and portions thereof are disclosed in several U.S. Pats., for example Nos. 2,656,508; 2,985,830; and 3,259,842 (each in class 324-71). A significantly important portion of such Coulter type of apparatus is the minute scanning aperture or scanning ambit or sensing zone relative to or through which pass and are detected single particles at a rate often well in excess of one thousand per second. Because of the physical parameters of the scanning aperture and particle concentration, there frequently results the coincidence of two or more particles in the scanning ambit. As a result, there effectively is detected and counted only one particle, not two or more. Such loss of count condition is identified as primary coincidence.

On the other hand, two or more small particles, which individually would not be counted because of their small size, can coincide to produce a pulse which is counted as a single (non-existent) larger particle. Such gain of count condition is identified as secondary coincidence.

Although such coincidence count conditions are random in time, they follow a statistically ascertainable form, from which curves, tables, and formulae are obtainable. A relatively simple one of such formulae is: $n = N - kN^2/2$; in which $n$ = the detected number of particles, or raw count;
$N$ = the true, or corrected count; and
$k$ = a constant which relates to the physical parameters of the scanning elements of the analyzing apparatus.

Heretofore, the operator of a "Coulter Counter" would obtain the raw count by analysis of a suspension of particles and then would refer to a coincidence correction chart which presented the corrected count for a selection of conditions.

Although the use of charts often can provide an accurate result, it is both time consuming and prohibits the fully automatic recording and processing of the corrected counts. Also, of course, the accumulating count during analysis is uncorrected. Different charts must be used with apertures of different sizes, and different counting procedures, such as the position of the counting threshold level in relation to the particle size distribution.

The use of analog, non-linear meters and/or elements in the output stage of a "Coulter Counter" also has been accomplished with limited success; however, in many uses a direct reading digitalized output greatly is to be preferred.

A recently developed, automatic digitalized system and method for coincidence correction, that yields a continuously corrected true count N, is the subject of U.S. Pat. No. 3,626,164. According to the therein described invention, various amounts of the addends are periodically generated by a somewhat complex arrangement of counters and are periodically applied to the continuously accumulating augend count of the particles to yield the true count. Although such method and apparatus provide a distinct advantage over the prior art, they possess the basic limitation of being programmed to a specific correction factor constant $k$, which itself is tied to the physical parameters of the detecting apparatus, such as the size and volume of the detecting aperture. Hence, changes, such as in aperture size, require program changes in the correcting apparatus. Additionally, this somewhat complex arrangement presents a purchase and maintainence cost which must be considered from a commercial sense.

Considerable research effort has been devoted to the phenomena of particle coincidence in a "Coulter Counter". A few of the many publications resulting from such consideration are next listed: Wales, M. and Wilson, J. N., Theory of Coincidence in Particle Counters, *Review of Scient. Instruments*, Vol. 32, Nr. 10, pp. 1132–1136. Oct. 1961; Princen, L. H. and Kwolek, W. F., Coincidence Corrections for Particle Size Determination with the Coulter Counter, *Review of Scientific Instruments*, Vol. 36, Nr. 5, pp. 646–653, May 1965; Strackee, J., Coincidence Loss in Bloodcounters, *Medical and Biological Engineering*, Vol. 4, pp. 97–99, 1966; Princen, L. H., Improved Determination of Calibration and Coincidence Correction Constants for Coulter Counters, Review of Scient. Instruments, Vol. 37, Nr. 10, pp. 1416–1418, Oct. 1966; Edmundson, I. C., Coincidence Error in Coulter Counter Particle Size Analysis, *Nature*, Vol. 212, pp. 1450–1452; and Bennert, W. and Hilbig, G., The Theory of the Coincidence Error for Digital Particle Size Analysis, Staub-Reinholt, *Luft*, Vol. 27, Nr. 4, April 1967.

K is the critical volume (in terms of the unit volume of fluid passed through the aperture during a particle count, for instance 1 ml) defined by the scanning aperture of a Coulter type particle analyzer. Unfortunately, the critical volume is not a fixed amount for any one aperture, and certainly is not the same under varying input conditions. One of the variables that goes into the determination of the critical volume is the electric field in the immediate vicinity outside of the scanning aperture, which must be included in what has been termed the "scanning ambit" of the particle detector. Such varying electric field is discussed in U.S. Pat. No. 3,668,531.

Although the Coulter type of particle analyzer, with its aperture form of scanning or sensing zone, is specifically described herein, other forms of particle analyzers, such as those operating with light or acoustic energy and having optical or acoustic sensing zones are encompassed by the invention herein, to the extent that these other types of particle analyzers are subject to particle coincidence in their sensing zones.

CROSS REFERENCE TO RELATED PUBLICATION

Reference may be made to and same is expressly incorporated herein: "Theory Of Coincidence Counts, And Simple Practical Methods Of Coincidence Count Correction For Optical And Resistive-Pulse Particle Counters" by H. Bader, H. R. Gordon, and O. B. Brown; *Review Of Scientific Instruments*, October 1972; H. Bader being the inventor herein.

SUMMARY OF THE INVENTION

If K is ascertainable for a given set of instrumental conditions, and if secondary coincidence is known to be negligible, then the true number N of particles in the suspension can be determined accurately by the equation $N = 1/K \ln(l-Kn)$, where ln is the natural logarithm.

By creating at least two related raw counts $n$ and $n_i$, as at least two physically derived counts, there can be developed a mathematic function relationship by which the scanning constant $k$ of a Coulter type of particle analyzer can be factored out and a resultant equation obtained. The resultant equation is employable in operating upon the input $n$ and $n_i$ raw counts for generating the ultimately desired corrected count $N_t$.

The invention encompasses method and apparatus by which the raw counts are developed:

a. by passing the sample volume through two or more different scanning apertures having known ratios of their critical volumes to obtain $n$, $n_i$, $n_j$, etc.;

b. by passing two or more different dilutions of known dilution relationship of the sample through a single scanning aperture to obtain $n$, $n_i$, $n_j$, etc.; and c. by a variation of (b) form a resultant from $n$ and $n_i$ which defines the critical volume K rather than the corrected count $N_t$.

BRIEF DESCRIPTION OF THE DRAWING

FIG. 1 is a diagrammatic view illustrating the profile of one form of scanning wafer having particles passing through its aperture along three different paths, with the resulting electric pulses being shown adjacent the aperture profile;

FIG. 2 is a block diagram of coincidence correction apparatus according to one embodiment of the invention;

FIG. 3 is a block diagram of another embodiment of the invention;

DESCRIPTION OF THE PREFERRED EMBODIMENTS

Figure 4:
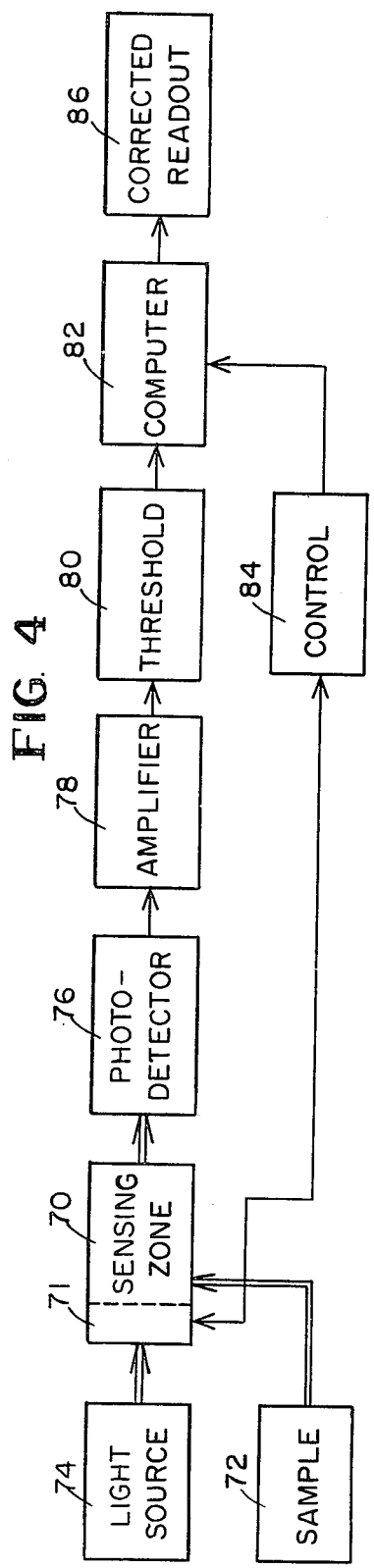
FIG. 4 is a block diagram of an optical embodiment of the invention.

Recent work done at the University of Miami has produced a more useful equation as a basis for coincidence correction, derived from Poisson distribution of pulse generation. The equation is written as a series with some unknown terms, but of known mathematical structure. If there are no significant count losses in the instrument electronics, and n is the registered count resulting from N particles passing through the effective or sensing zone of volume K, then:

(1) $n = N - K/2! (N^2 - x^2) + K^2/3! (N^3 - y^3) - K^3/4! (N^4 - z^4) + \ldots$ $x$, $y$ and $z$ are unknown linear combinations of numbers of particles in different size ranges, which give rise to spurious secondary coincidence counts.

The series (1) converges rapidly when the product KN is substantially smaller than unity, which most often can be realized in particle counting instruments. One then can achieve very good count correction by considering only the first correction term $K/2(N^2-x^2)$, and neglecting all subsequent terms. If the second term $K^2/6(N^3-y^3)$ is not negligible in terms of the required accuracy, it also must be considered, neglecting subsequent terms. In principle any desired number of terms can be considered by acquiring the necessary information by varying procedural and/or instrumental parameters. When secondary coincidence is negligible, which very often is true in practice, then we can set $x=y=z=0$. Equation (1) then reduces to:

(2) $n = 1/K (1 - e^{-KN})$.

If K also is ascertainable, reversion of (2) yields:

(3) $N = 1/K \ln (l-Kn)$, where ln is the natural logarithm.

In FIG. 1, there is illustrated the sectional profile of a typical wafer 10 in a "Coulter Counter" counting and sizing apparatus having an aperture 12 therein. The structure is shown simply as a cylindrical bore with sharp edges 14 and 16. When aperture current is established by electrodes (not shown) on opposite sides of the wafer, electricity flows through the aperture from one side to the other, as for example from the left side to the right. The wafer 10 bearing the aperture 12 is immersed in the sample fluid or electrolyte, but no symbols are used to illustrate this in order to keep the view simple. As the electric current passes through the liquid, the electric current density within and adjacent the aperture is different than it is throughout other parts of the bodies of fluid through which the current passes. In the aperture itself, the electric current density will vary from location to location. The current density at the corners 14 and 16 will be much greater than anywhere else.

Some of the isopotential lines are illustrated in FIG. 1. These lines are shown to be perpendicular at every point where they touch the outer surface of the wafer 10, being transverse of the bore 12 at 18, slightly bulging out at the ends 20, and being quite arcuate at the outer surface of the bulge 22. Taken as a whole, the volume of fluid which is within as well as close to the physical limits of the aperture defines a volume that is effected by the concentration of the degree of density of the electric current so as to define a scanning ambit or critical volume K through which passing particles cause a resistive change and generate detectable pulses. Although the current density in the aperture 12 generally is greater than it is outside of the aperture, the current density is a maximum at the corners 14 and 16, where the electric current turns the corner, so to speak, to enter the aperture 12 and, therefore, is greater than in the center of the aperture.

Consider now, three particle paths A, B and C through the aperture from left to right along the broken lines shown in FIG. 1. The first particle A traverses approximately the center of the aperture with the physical stream of liquid and, as it passes from left to right through the influence of the increased current density, its maximum effect upon the resistance of the scanning ambit of the aperture is near the center of the aperture where the isopotential lines 18 are closest and parallel to each other. Considering the graph of the resulting electrical pulse, which may be assumed to have been made by some detecting means as will be discussed with reference to FIGS. 2 and 3, the pulse is shown as A, its maximum amplitude AMP.A is in its center, and is proportional to the size of the particle A. The duration of the pulse is equal to the time which the particle was within the ambit of the aperture, that is, within its electrical influence. This is considerably more than L, the length of the aperture 12, since, as noted, there is a convex bulge of relatively high electric current density outside of the geometric confines of the aperture.

If all particles follow paths similar to the path A, or quite close to the center of the aperture 12, then all of the resulting pulses would have the apperance of the pulse A, differing only in amplitude, which would be particle size related. It will be appreciated that the dimensions are exaggerated in the view to provide a better understanding of the theory of the discussion. The total duration of the pulse is commonly of the order of 20 to 40 micro-seconds.

All particles do not pass through the aperture 12 along paths similar to path A. Some approach along paths considerably displaced from the axis of the physical stream of liquid and are drawn into the aperture just before the stream enters the entrance to the aperture 12, as the path C, or even closer to the entrance, as the path B. Moreover, more than one particle can reside within and move through the scanning ambit at the same time or at least in overlapping times. For purposes of this disussion and the wave forms illustrated in FIG. 1, the particles A and B which traverse the paths A and B are to be assumed to be identical in size; whereas, the particle C is twice that size and normally should have an amplitude AMP.C twice that of AMP.A, if it and particle A were to pass along the path A at different times. However, as the particle B moves through the ambit of the aperture 12, it passes close to the corner 14, where the current density is a maximum, and the effect is as though the resistance of the aperture 12 is increased at that point. Accordingly, there will be a peak 24 of amplitude AMP.B at the beginning of the pulse B.

As the particle B enteres the aperture 12, it moves into the influence of the electric current region 18, where the density is quite uniform so that the corresponding amplitude of the pulse B will be that of AMP.A as shown in its part 26. As the particle B along the path B leaves the aperture 12, it passes close to the corner 16 through a region of high current density and, therefore, another peak 28 is generated, which would be larger than the part of the pulse indicated at 26.

The particle C, which is twice the size of particle A or B and therefore equal to the sum of their volumes, is shown traversing the path C, which produces the pulse C having a peak amplitude 30 which, while not twice that of the AMP.B of the peak 24 is more than twice AMP.A. The top of the pulse C is neither a smooth curved dome as that of pulse A, nor distinctly dual peaked, as in pulse B, nor are any of the pulses flat topped; hence, there is no single profile which can be used easily to distinguish a particle pulse generated by a single particle from a resulting waveform generated by the coincidence of two or more particles in the aperture ambit. This conclusion holds true, even though the pulse A profile is the most desirable, since coincident derived waveforms can have the profile of pulse A as well as pulse B or C, as next will be detailed with respect to the waveform A+B.

If the particles A and B were to traverse the aperture ambit at the same time along their respective paths A and B, there would result the generation of a waveform or pulse A+B as shown in FIG. 1. Such pulse would be the point by point sum of the pulses A and B, as if plotted in a superimposed, well known manner. The striking similarity between the pulse C and the pulse A+B, though somewhat unique, leaves no doubt in the fact that two particles can and do create the electronic pulse image of only one particle even though the different size. Likewise, three and more particles can coincide within the ambit of the aperture and simulate only one particle. Thus, in counting and size distribution studies accomplished by a "Coulter Counter" there will develop a loss or gain of one particle count each time a pulse A+B is generated by the time coincidence of particles in the aperture. If the particle pulses A and B are both above the minimum threshold value for counting of pulses, then pulse A+B will result in a primary coincidence condition, i.e., a loss of count; whereas, if the particle pulses A and B both are below the minimum threshold and their coincidence pulse A+B is above that threshold, a secondary coincidence count gain results.

The passage of the particles A and B need not be simultaneous to create a coincidence count condition. If two particles are slightly separated in time, there will be formed a dual peaked pulse, similar to the pulse B. Unfortunately, unless the valley 26 between the peaks 24 and 28 of a profile like pulse B is low enough to cross a low threshold, or the slopes are otherwise distinguishable, pulse analysis is usable to distinguish between a pulse B derived from one or more particles and will report only one particle count; hence, a coincidence count condition.

As stated hereinabove, with reference to equations (2) and (3), if the critical volume, K, or the scanning constant, k, could be ascertained, then the problem of coincidence loss or gain would be resolved more easily and accurately than heretofor. Such is the goal of the method and apparatus according to FIGS. 2 and 3, which eliminate the first correction term of equation (1).

With reference to FIG. 2, consider an arrangement in which a common source of particle sample 32 feeds into two aperture arrangements 34, 36, which respectively, apply their output pulses to amplifiers 38, 40, threshold circuits 42, 44, and accumulators 46, 48. Details of plural aperture setups are disclosed in U.S. Pat Nos. 3,444,463; 3,444,464; and 3,549,994 (class 324-71). It is to be assumed herein that the "aperture" blocks contain not only the aperture wafer 10 and aperture 12, but also the aperture tubes, beakers, sample moving and measuring structures, electrodes, etc., all well known and disclosed in the patents cited herein.

If the particle analyzer is other than of the Coulter type, the blocks 34 and 35 will contain their appropriate sensing zone arrangements. Hence, the term "aperture" as used herein is not limiting.

For the first embodiment of the invention, both method and apparatus, consider the sensing zones or apertures in the blocks 34 ane 36 of FIG. 2 to be of different volumes, with the "aperture" of 36 to be 1/R times the critical volume of the "aperture" of 34. By substitution into equation (1) and using a single correction term:

$$4\quad n = N - K/2\ (N^2 - x^2)$$

and $$5\quad n_R = N - K/2R(N^2 - x^2),$$

wherein the uncorrected or raw counts from the apertures 34 and 36 are, respectively, n and $n_R$, and their scanning constants are $k$ and $k/R$, respectively. The correction terms can be factored out by: multiplying equation (5) by R; subtracting equation (4); and solving for N, which is identified as $N_R$. There results:

$$6\quad N_R = \frac{Rn_R - n}{R - 1}$$

Equation (6) does not contain any constants of calibration nor does it depend upon knowledge of the critical volume per se and thereby it meets the basic needs and principles of the invention. Moreover, such mathematic function can be built into a computation unit, such as represented by a computer block 50 in FIG. 2, which receives the raw counts n and $n_R$ at inputs 52 and 54 from the accumulators 46 and 48, to provide from its output 56 a coincidence corrected count for receipt by any one or more of known readout devices, represented by a corrected readout device 58.

The computational unit 50 in FIG. 2 as well as the "computer" blocks in FIGS. 3 and 4 can be any of many well known general purpose computers which can be connected to the accumulators, or even can include the accumulator stages. The programmed data processor line of minicomputers by Digital Equipment Corporation has been employed successfully for receiving and processing data from various Coulter Counter particle analyzers. A PDP-8E minicomputer can meet the needs of the computational processing hereinafter set forth. Of course, computation can be accomplished by pencil and paper as well as by a hand-operated calculator.

It will be appreciated that the critical volume ratio determines the numeric multiplier R. If, for example, the ratio was 2:1, then $R=2$ and equation (6) resolves into:

$$7\quad N_2 = 2n_2 - n.$$

Notwithstanding the fact that the apertures 34 and 36 have two different critical volumes, the same amount of sample is to flow through each; hence, the true count of the particles passing therethrough should be the same for each aperture, were it not for the coincidence phenomena, which operates differently upon the different apertures.

In the embodiment described with reference to FIG. 2, there is the assumption that apertures having known relationships with respect to their critical volumes are obtainable; whereas, it is also a basic premise of the problem that the actual volume, and therefore the critical volume of an aperture is not ascertainable. The named assumption is not rendered impossible or even impractical by the named premise, since one does not have to ascertain the actual volumes to be able to empirically construct two apertures having a known ratio of their (unknown) volumes. Nevertheless, the use of two apertures and two parallel channels of components presents cost, space, maintenance and other considerations which would be reduced if only one aperture was needed. Such is accomplished in the next described embodiment of FIG. 3.

With reference to FIG. 3, the aperture 34, amplifier 38, threshold circuit 42, accumulator 46 and readout device 58 can be the same as those same named elements of FIG. 2. A computer 62 can be the same basic structure as that of the computer 50; however, it will be programmed to a different mathematic function, which is next described, and it receives only one raw count at any one time. The sample input arrangement provides for two different dilutions of the same sample and of a known dilution ratio. The two dilutions only are digrammatically shown in two containers 32 and 64 and their method of formation can be by any manner by which their relative dilutions can be ascertained. For example, the sample 32 can be analyzed and returned to the "container" 32 and there be diluted to become the sample 64.

For the description herein it is assumed that sample 64 is diluted by a factor r with respect to sample 32, by diluting v ml of sample 32 with $\Delta v$ ml of particle-free diluent; hence:

$$8\quad r = 1 + \Delta v/v.$$

A flow control means 66 will determine which sample is being received by the aperture at any given time and will insure that, for every ml of sample 32 producing a raw count n, bml of diluted sample 64 will be passed, thus producing the raw count $n_r$. Using equation (1):

$$9.\quad n = N - K/2\ (N^2 - x^2)$$

and $$10\quad n_r = \frac{bN}{r} - \frac{bK}{2} \cdot \frac{N^2 - x^2}{r^2}.$$

Solving simultaneous equations (9) and (10) for N, which is called $N_r$, the corrected count becomes:

$$11\quad N_r = \frac{\frac{r^2}{b} n_r - n}{r - 1},$$

which is the mathematical function built into the computer 62.

If, for instance, $r = 2$ (1:1 dilution), and $b = 4$ (pass 1 ml of sample 32, and 4 ml of diluted sample) then equation (11) becomes:

$$12.\quad N_r = n_r - n.$$

In this case, the computational procedure is very simple. First, the raw count from the 4 ml of sample 64 is accumulated, and then the raw count from 1 ml of sample 32 is subtracted. Such mathematics can be accomplished easily with an up-down counter which has its add and subtract modes determined by whichever of the samples is being provided by way of the flow control means 66. A linkage 67 symbolizes such mode control between the flow control means 66 and the computer 62, which can be an up-down counter.

The embodiment of FIG. 3 has proven to be superior to that of the FIG. 2 embodiment with respect to instrument dead-time count losses. Well known is the fact that counting instruments require a finite amount of recovery time after processing one count and before the next count can be recognized for processing. If such next particle count falls within the recovery time, it is lost; hence, a dead-time count loss. Experimentation has verified that such form of dead-time count loss does not adversely affect, i.e. is computationally eleminated by the dilution method and apparatus of FIG. 3, but does affect the accuracy of the FIG. 2 embodiment. The FIG. 3 embodiment itself posseses certain practical drawbacks in the form of the time and equipment necessary for making two precise dilutions, passing determined amounts of the sample, and the time for processing the two dilutions sequentially.

The critical volume K can be derived by use of the equation (3) and the dilution method and apparatus (FIG. 3), wherein the raw count n is obtained from the sample 32 and the raw count $n_r$ is obtained from the sample 64 which has been diluted by the factor r. The general solution of equation (3) yields the following series, which converges when $F<1$.

$$(13)\ K = \frac{3F}{n_r} \left[ 1 + (r-2)F + \frac{(r-2)(5r-7)F^2}{4} + \cdots \right]$$

$$\text{where } F = \frac{2}{3} \cdot \frac{m_r - n}{r(r-1)n_r}.$$

When r = 2, equation (13) simplifies as:

$$(14)\ K = \frac{2n_2 - n}{n_2^2}.$$

The value of K will be in ml, if n and $n_r$ are counts from 1 ml of sample.

The above determination of the critical volume $K$ assumes that secondary coincidence count gains and instrument dead-time count losses are negligible.

In cases where elimination of the first correction term in equation (1) is insufficient for obtaining the required accuracy, the second correction term can be eliminated by obtaining an additional count by use of a third aperture or a third dilution.

By the dilution method of FIG. 3, the particle counts are taken on the original suspension, on a dilution by factor r and on a dilution by factor S, where $1<r<s$. Let the counts be respectively n, $n_r$, $n_s$. Solving the three simultaneous equations of type (1), to obtain the corrected count $N_{rs}$:

$$15\ N_{rs} = \frac{1}{s-r} \left[ \frac{S^3 n_s}{s-1} - \frac{r^3 n_r}{r-1} + \frac{(s-r)n}{(s-1)(r-1)} \right].$$

In FIG. 3, the sample 64 is to be assumed to be the original suspension sample 32 diluted by the factor $r$, and that a sample 64' is diluted by the factor s.

By the aperture change method of FIG. 2, the raw counts are taken with three different apertures, with aperture volumes K, K/R and K/S. The counts are respectively n, $n_R$ and $n_S$. Solving the corresponding simultaneous equations (1), to obtain the corrected count $N_{RS}$:

$$16\ N_{RS} = \frac{1}{S-R} \left[ \frac{S^2 n_S}{S-1} - \frac{R^2 n_R}{R-1} + \frac{(S-R)n}{(S-1)(R-1)} \right].$$

In FIG. 2, the apertures 34 and 36 would have the critical volumes K and K/R, respectively, and an aperture 36' in a path 36'-54' would have the volume K/S. Such path 36'-54' also would contain a series connected amplifier 40', threshold 44' and accumulator 48'(none of which are specifically illustrated), with the output path 54' feeding the count $n_S$ to the computer 50.

The teaching of this invention also can be applied to multi-channel analysis in which each aperture would have a plurality of parallel connected threshold circuits, each threshold supplying particle pulses to its own accumulator, to define the multi-channels. For example, consider only two channels, each having a different threshold value setting. By use of equation (11), the formulas for the two channels can be written and then subtracted to form an expression for the number of particle ΔN in a given size range:

$$17\ \Delta N = \frac{r^2 \Delta n_r - \Delta n}{r-1}.$$

Thus, in multichannel analysis, coincidence correction for each channel is accomplished by substituting $\Delta N_r$ for $N_r$.

In the description and explanation up to this point, the Coulter type of resistive scanning aperture was the embodied example of the sensing zone through which the particles flow. It should be clearly understood that "sensing zone" is not limited to a Coulter type of sensing aperture and that, as employed herein (including FIGS. 2 and 3), the term "aperture" is not to be limiting and encompasses other forms of scanners, including optical scanners.

In optical particle counting, the suspension of particles is in a jet stream which passes through a known volume K that is illuminated by an optical system. An optical sensor or photodetector "views" the illuminated volume and produces a signal pulse whenever a particle passing through the volume scatters the light therein. A great variety of technical means can be used to provide the different raw counts n, $n_r$, $n_s$, or n, $n_R$, $n_s$, etc., for calculation of the coincidence corrected count N according to the basic teachings of the invention herein.

Just as in FIGS. 2 and 3, there can be simultaneous as well as sequential optical counting arrangements and methods. A sequential counting can be provided with a single optical sensor, as single sensing volume K and a single jet stream, wherein sequentially applied different dilutions of the particle suspension provide the different raw counts as in FIG. 3.

As will be described with reference to FIGS. 4–6, a sequential counting arrangement can be provided by sequentially changing the sensing volume K of a single optical sensor, by effectively changing the size of the optically projected beam of light (its slit width) into the jet stream.

Simultaneous counting can be accomplished optically by use of plural sensors of different volumes and employing the arrangement of FIG. 2.

According to the arrangement of FIG. 4, an optical sensing zone 70 receives a stream of particles from the sample source 72 and a beam of light from a light source 74 according to well known arrangements. The sensing zone 70 includes an arrangement 71 for changing its sensing volume K in a predetermined manner, whereby two or more different sensing volumes can be formed sequentially. Preferably, the duration for which each sensing volume is operative is automatically controlled, and the change of volumes is cyclic, as will be described with reference to the embodiments in FIGS. 5 and 6.

As a consequence of a sequentially changing sensing volumes, the sample concentration and light beam otherwise remaining constant, a photodetector 76 will receive sequential trains of pulses, with each train representing the particles sensed during the presence of its respective sensing volume. By way of an amplifier 78 and a threshold 80, a computer 82 will receive sequential groups of pulses that each contain a number of pulses whichis proportional to the particles sensed during the sequentially generated different sensing volumes.

A control device 84 is provided and, depending upon the nature of the sensing volume changing arrangement 71, detects and also could determine which sensing volume is present, the time of change and the cyclic parameters. The detection of the change from one sensing volume to another is applied by the control device to the computer to control its operation in a manner depending upon its program function, as will be clarified subsequently. The output from the computer will be the coincidence corrected readout as symbolized by the block 86 in FIG. 4.

For a sequential counting of particles using two different sensing volumes $Rv$ and $v$, with $v$ being the smaller volume and a timing cycle of T seconds, which commences with illumination of the sensing volume $v$ for a time $RT/R+1$, followed by illumination of the sensing volume $Rv$ for a time $T/R+1$, the corrected count readily can be obtained if the computer 82 is an up-down counter and the control device places the counter 82 in the up (add) mode during the time of volume $v$ and then switches the counter to the down (subtract) mode during the time of volume $Rv$.

Let

F = fluid volume flow rate through the sensing volume (unit volumes per second)
T = time cycle (seconds)
C = number of cycles in counting period
n = registered count after C cycles
$N_R$ = calculated number of particles in unit volume of fluid
R = critical volume ratio multiplier
$n_R$ = count per unit volume of suspension during $v$
$n_o$ = count per unit volume of suspension during $Rv$.

By substitution into equation (6):

$$18 \quad N_R = \frac{Rn_R - n_o}{R-1}.$$

Also, $$N = \frac{FCT(Rn_R - n_o)}{R+1};$$

hence, $$19 \quad N_R = n \frac{R+1}{(R-1)FCT}.$$

A statistical error calculation shows that the larger that R becomes, the closer $N_R$ is to the true number of particles. $R=3$ is quite good.

The relative ease by which this facet of my invention can be implemented is demonstrated by the embodiments of the sensing volume changing arrangements 71 shown in FIGS. 5 and 6 and their corresponding Tables A and B presented herein below.

Figure 5:
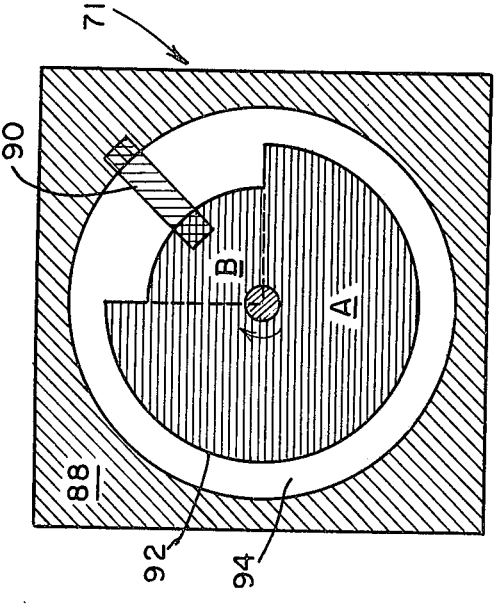
FIG. 5 is a diagrammatic view of one form of a sensing volume changing arrangement useful in the embodiment of FIG. 4.

As shown in FIG. 5, which is only diagrammatic, a mounting member 88 is interposed into the path of the beam of light 90, preferably just ahead of the intersection of the beam 90 and the jet stream of the sample suspension. Mounted for rotation within the member 88 is a disc 92 which has two segments A and B of different radius and different subtended angles A and B, respectively. The disc 92 and the peripheral portions of the member 88 are optically opaque, as shown by shading in FIG. 5. The entire circular central area of the member 88 is optically transparent and in fact need not be present physicalllly, except for rotative support of the disc 92. Hence, there is fomred an optically transparent annulus 94 between the disc 92 and the member 88. Since the radius of the segment B is less than that of the segment A, that portion of the annulus by the segment B is wider. Accordingly, as the disc rotates, there will be two different cross sectional areas of the light beam 90 which are permitted to pass through the sensing volume changing arrangement 71, into the jet stream and toward the photodetector 76. Effectively, the slit width is automatically being precisely changed.

Since the total sample volume is to remain constant for each of the sequential counting periods, and the cross section of the passed beam 90 bears a direct relationship to the critical volume, the duration of each segment A and B is determinable. Assuming a constant flow rate of the sample suspension (at least for each cycle of the disc 92) and a uniform rotation of the disc, the angles A and B are definable for any critical volume ratio multiplier, as shown in Table A.

TABLE A

| R | $\frac{R+1}{R-1}$ | $\frac{R}{R+1}$ | $\frac{1}{R+1}$ | A | B |
|---|---|---|---|---|---|
| 2 | 3 | 2/3 | 1/3 | 240° | 120° |
| 3 | 2 | 3/4 | 1/4 | 270° | 90° |
| 4 | 5/3 | 4/5 | 1/5 | 288° | 72° |
| 5 | 3/2 | 5/6 | 1/6 | 300° | 60° |

During the presence of segment A, the control device 84 places the up-down counter 82 in the adding mode, and during segment B the counter is put into the subtract mode.

Figure 6:
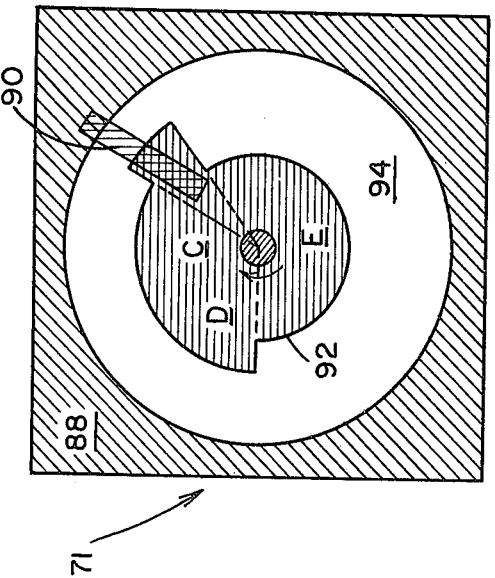
FIG. 6 is a diagrammatic view of a variation of the arrangement of FIG. 5.

If three different sensing volumes are required, the arrangement of FIG. 6 can be employed. As shown therein, three disc segments C, D and E are provided, so that the intersection of the beam 90 with three sequentially different widths of the annulus 94 are obtained.

The sensing volumes are $v$, $Rv$, and $Sv$, with $v<Rv<Sv$, with $n_S$ being the count during volume $Sv$. The time cycle begins with illumination of sensing volume $v$ during time $$\frac{(S-R)T}{X},$$

where $X = S^2(R-1) + R^2(S-1) + S - R$,
followed by illumination of sensing volume Sv during time $$\frac{S^2(R-1)T}{X}.$$

The cycle is completed by illumination of sensing volume Rv during time $$\frac{R^2(S-1)T}{X}.$$

The basic equation is:

$$20 \quad N_{RS} = \frac{S^2(R-1)n_S + (S-R)n_o - R^2(S-1)n_R}{(S-R)(S-1)(R-1)}.$$

Also, $$N = \frac{FCT}{X}[S^2(R-1)n_S + (S-R)n_o - R^2(S-1)n_R];$$

hence, $$21 \quad N_{RS} = n\frac{S^2(R-1) - R^2(S-1) + S - R}{FCT(S-R)(S-1)(R-1)} = \frac{N}{FCT}.$$

$N_{RS}$ is a better approximation to the true number of particles than $N_R$.

The sequence of the segments C, D and E is not critical; however, during the presence of the segments C and E, the control device 84 places the computer 82 into the addition mode for the counts $n_o$ and $n_S$; whereas, it is in the subtraction mode for the counting of $N_R$, during the presence of segment D in the optical beam 90. From a comparison of Tables A and B it will be noted that the parameters are each based upon their individual conditions, but are founded upon equations (6), and (20).

TABLE B

| R | S | $\frac{(S-R)T}{X}$ | $\frac{R^2(S-1)T}{X}$ | $\frac{S^2(R-1)T}{X}$ | C | D | E |
|---|---|---|---|---|---|---|---|
| 2 | 4 | 1/15 | 6/15 | 8/15 | 24° | 144° | 192° |
| 2 | 6 | 1/15 | 5/15 | 9/15 | 24° | 120° | 216° |

Although several specific formulas for $N_r$ and K have been presented hereinabove for various $n$ and $n_r$ origins and relationships, such formulas being programmed into the computers in FIGS. 2–4, it is possible that other equally valid formulas for $N_r$ and/or K can be developed and then be applied with satisfactory results according to the methods and apparatus of the invention claimed herein. Accordingly, the specific formulas are only examples of a broader or generic group of mathematic function relationships between $n$ and $n_r$ which can be employed within the scope of the invention.

Furthermore, it will be recognized by those skilled in the art that, although the embodiments of the invention are described in connection with the Coulter type of particle analyzer and also a form of optical particle analyzer, it will apply equally well to any particle-counting apparatus which employs a sensing zone, whether this sensing zone is energized by an electric field, as in the "Coulter Counter", or by light, acoustic energy, or a magnetic field.

What is sought to be protected by United States Letters Patent is:

1. A method for use in the correction of primary and secondary coincident particle count variations in a particle analyzer of the sensing zone type comprising the steps of: generating a plurality of trains of particle pulses by passing at least one portion of a sample of particles through at least one sensing zone type of particle sensing zone arrangement, said step of generating the pulse trains including the step of developing each pulse train relative to the other pulse trains so that each pulse train has a different number of pulses by using at least one of a specific ratio, other than unity, of sample dilutions, sample volumes and sensing zone volumes in such a manner that the number of pulses in each train is in accordance with a coincidence count interrelated mathematic function relationship with the number of pulses in the other trains of pulses, in which the only unknowns in such relationship are the number of pulses in each train; the number of pulses in each train and said ratios being all of the mathematic factors required in the solving of a specific coincidence correction equation for a resultant coincidence corrected particle count.

2. The method according to claim 1 in which the sensing zone arrangement is caused to operate according to the Coulter method of particle sensing.

3. The method according to claim 1 in which the sensing zone arrangement is caused to operate according to optical sensing methods.

4. The method according to claim 1 in which said step of developing includes the passing of equal volumes of particle sample separately through at least two sensing zones the critical volumes of which having a known ratio R, and arranging pulse count accumulating of the trains of pulses such that the pulse count of each train comes solely from its sensing zone.

5. The method according to claim 4 in which said steps include employing the function $$N_R = \frac{Rn_R - n}{R - 1},$$

in which
  $N_R$ is the coincidence corrected count,
  R is the ratio of the critical volumes of the sensing zones, and $n$ and $n_R$ are the number of pulses from the sensing zones of critical volume ratio R.

6. The method according to claim 1 in which said step of developing includes the forming of at least two different dilutions of known dilution ratio of the particle sample and of the same volume, and passing such dilutions separately through a single sensing zone to separately develop the pulse trains for accumulating of their pulses.

7. The method according to claim 6 in which said steps include employing the function $$N_r = \frac{\frac{r^2}{b} \cdot n_r - n}{r-1},$$

in which
N_r is the coincidence corrected count,
b is the volume of the dilution,
r is the dilution ratio factor, and
n and n_r are the number of pulses separately resulting from the two dilutions.

8. The method according to claim 6 which further comprises the step of mathematically operating upon the accumulated pulses in terms of critical volume of the sensing zone and deriving as a resultant the critical volume.

9. The method according to claim 8 in which said step of mathematic operating employs the equation $$K = \frac{2n_2 - n}{n_2^2},$$

in which the dilution ratio r is 2 and therefore $n_r$ becomes $n_2$,
K is the critical volume of the sensing zone, and
n and $n_2$ are the number of pulses separately resulting from the two dilutions.

10. The method according to claim 1 in which said step of developing includes the sequential passing of volumes of particle sample separately through at least two sensing zones of the optic type, in which a beam of light projects through a stream of particles, the critical volumes of the sensing zones having a known ratio R, and arranging pulse count accumulating of the trains of pulses such that the pulse count of each train comes solely from its sensing zone.

11. The method according to claim 10 in which the critical volume ratio R is defined by effectively changing the slit width of the beam of light.

12. The method according to claim 11 in which said steps include employing the function $$N_R = n \frac{R+1}{(R-1) \, FCT},$$

in which
$N_R$ is the calculated number of particles,
n is the registered pulse count after C cycles,
R is the critical volume ratio multiplier,
F is the fluid flow rate through the sensing zone,
C is the number of cycles in the counting period, and
T is the time cycle.

13. A method for use in the determination of the critical volume of the sensing zone in a particle analyzer of the sensing zone type wherein coincident particle count variations occur, comprising the steps of: generating a first and a second train of particle pulses by passing two different dilutions of equal volumes of a sample of particles through the sensing zone of the particle analyzer, said step of generating the pulse trains including the step of developing each pulse train relative to the other pulse train by using a ratio, other than unity, of sample dilutions in such a manner that the number of pulses in each train are different from each other and provides an interrelated mathematic function relationship between the trains of pulses in terms of the critical volume of the sensing zone, in which the only unknowns in such relationship are the number of pulses in each train, and the number of pulses in each train and dilution ratio being all of the mathematic factors required in the solving of a specific critical volume equation for the critical volume of the sensing zone.

14. The method according to claim 13 in which said steps include employing the function $$K = \frac{2n_2 - n}{n_2^2},$$

in which the dilution ratio r is 2 and therefore $n_r$ becomes $n_2$,
K is the critical volume of the sensing zone, and n and $n_2$ are the number of pulses separately resulting from the two dilutions.

15. Apparatus for use in the correction of primary and secondary coincident particle count variations and thereby for obtaining a resultant coincidence corrected particle count for a particle analyzer of the sensing zone type, comprising: means for generating a plurality of trains of particle pulses, said generating means including at least one sensing zone arrangement and means for supplying at least one measured volume of a sample of particles for passage through the sensing zone arrangement for the development of pulses from each of the pulse trains; said generating means further including control means in interconnecting said sensing zone arrangement and said supplying means for controlling sample passage and particle pulse generation; said supplying means, sensing zone arrangement, and control means being intercoupled for establishing of at least one of the ratio, other than unity, of sample dilutions, sample volumes, and sensing zone volumes such that the pulse development results in a different number of pulses in each train and the trains possess a coincidence count interrelated mathematic function relationship with respect to the number of pulses in each train pertaining to their coincidence corrected count in terms exclusive of any other unknowns; and the number of pulses in each train along with the employed ratios provide all of the mathematic factors required in the solving of a specific coincidence correction equation for a resultant coincidence corrected particle count.

16. Apparatus according to claim 15 in which said sensing zone is a Coulter-type scanning aperture.

17. Apparatus according to claim 15 in which said sensing zone is of an optical type.

18. The apparatus according to claim 15 including accumulating means for accumulating separately the pulses from each of the pulse trains as output count signals in which said generating means includes a supply of the sample wherein the improvement comprises: at least two sensing zones, the critical volumes of which are of a known ratio R, said generating means being thus constructed and arranged with respect to said controlling means for the passing of equal volumes of the particle sample separately through said sensing zones, and determining the mode of accumulating by said accumulating means, such that the pulses of each train comes solely from its sensing zone.

19. The apparatus according to claim 18 in which computation means is provided to perform the mathematic operation $$N_R = \frac{Rn_R - n}{R-1},$$

in which, $N_R$ is the coincidence corrected count,
R is the ratio of the critical volumes of the sensing zones, and
$n$ and $n_R$ are the number of pulses from the sensing zones of critical volume ratio R.

20. The apparatus according to claim 15 including accumulating means for accumulating separately the pulses from each of the pulse trains as output count signals in which said sensing zone arrangement has only a single sensing zone, wherein the improvement comprises: said supplying means includes means for the forming of at least two different dilutions of known dilution ratio of the particle sample and of the same volume for the passing of such dilutions separately through the single sensing zone, to separately develop the pulse trains for the accumulating by said accumulating means.

21. The apparatus according to claim 20 in which computation means is provided to perform the mathematic operation $$N_r = \frac{\frac{r^2}{b} \cdot n_r - n}{r-1},$$

in which $N_r$ is the coincidence corrected count,
$b$ is the volume of the dilution,
$r$ is the dilution ratio factor, and
$n$ and $n_r$ are the number of pulses separately resulting from the two dilutions.

22. The apparatus according to claim 20 in which computation means further is provided for mathematically operating upon the accumulated output count signals in terms of the critical volume of the sensing zone and thereby for deriving as a resultant the critical volume.

23. The apparatus according to claim 22 in which said computation means is constructed to perform the mathematic operation $$K = \frac{2n_2 - n}{n_2^2},$$

in which the dilution ratio is 2 and therefore $n_r$ becomes $n_2$,

K is the critical volume of the sensing zone, and
$n$ and $n_2$ are the number of pulses separately resulting from the two dilutions.

24. Apparatus according to claim 20 in which computation means is coupled to receive the trains of pulses, wherein the improvement comprises: said means for controlling sample flow is linked to said computation means for controlling its operation, and said computation means comprises an up-down counter.

25. The apparatus according to claim 15 in which said generating means includes a supply of the sample and is arranged to sequentially define at least two sensing zones of the optic type in which a beam of light projects through a stream of particles, the critical volumes of the sensing zones are of a known ratio R, said generating means being thus constructed and arranged with respect to said control means for the passing of volumes of the particle sample separately through said sensing zones, such that the pulses of each train comes solely from its sensing zone.

26. Apparatus according to claim 25 in which computation means is coupled to receive the trains of pulses, wherein the improvement comprises: said control means is coupled between said sensing zone arrangement and said computation means, for at least detecting the then present critical sensing volume and thereby for controlling the operation of said computation means.

27. Apparatus according to claim 26 in which said computation means is an up-down counter.

28. The apparatus according to claim 25 in which said generating means includes means for changing the critical volume ratio by changing the slit width of the beam of light.

29. The apparatus according to claim 28 in which computation means is provided to perform the mathematic operation $$N_R = n \frac{R+1}{(R-1) FCT},$$

in which $N_R$ is the calculated number of particles,
$n$ is the registered pulse count after C cycles,
R is the critical volume ratio multiplier,
F is the fluid flow rate through the sensing zone,
C is the number of cycles in the counting period, and
T is the time cycle.

30. The apparatus according to claim 28 in which the means for changing the critical volume ratio comprises a rotatable disc having a plurality of different segments of different radius and subtended angles, for determinably intercepting the beam of light so as to change its cross section prior to its projection into the stream of particles.

31. Apparatus for use in the determination of the critical volume of the sensing zone in a particle analyzer of the sensing zone type wherein coincident particle count variations occur, comprising: means for generating a first and a second train of particle pulses, said generating means including one sensing zone and supply means for supplying two different dilutions of equal volumes of a sample of particles sequentially through the sensing zone of the particle analyzer, said supply means and sensing zone arrangement being intercoupled for establishing a ratio, other than unity, of sample dilutions and a different number of pulses in each of the pulse trains such that an interrelated mathematic function relationship is established with respect to the number of pulses in each train pertaining to the critical volume of the sensing zone, in which the only unknowns in such relationship are the number of pulses in each train, and the number of pulses and said ratio being all of the mathematic factors required in the solving of a specific critical volume equation for the critical volume of the sensing zone.

32. The apparatus according to claim 31 in which computation means is provided to perform the mathematic operation $$K = \frac{2n_2 - n}{n_2^2},$$

in which the dilution ratio is 2 and therefore $n_r$ becomes $n_2$,

K is the critical volume of the sensing zone, and
$n$ and $n_2$ are the number of pulses separately resulting from the two dilutions.

* * * * *